(12) United States Patent
Bengs et al.

(10) Patent No.: US 6,703,048 B1
(45) Date of Patent: Mar. 9, 2004

(54) SPHERICAL MICROPARTICLES CONTAINING LINEAR POLYSACCHARIDES

(75) Inventors: Holger Bengs, Frankfurt (DE); Jürgen Grande, Bad Soden (DE); Arnold Schneller, Messel (DE); Gitte Böhm, Frankfurt (DE)

(73) Assignee: Celanese Ventures GmbH (DE)

( * ) Notice: Subject to any disclaimer, the term of this patent is extended or adjusted under 35 U.S.C. 154(b) by 0 days.

(21) Appl. No.: 09/486,357

(22) PCT Filed: Aug. 20, 1998

(86) PCT No.: PCT/EP98/05297

§ 371 (c)(1),
(2), (4) Date: Apr. 14, 2000

(87) PCT Pub. No.: WO99/11695

PCT Pub. Date: Mar. 11, 1999

(30) Foreign Application Priority Data

Aug. 28, 1997 (DE) .......................... 197 37 481

(51) Int. Cl.⁷ .......................... A61K 9/14; A61K 9/16; B01J 13/00
(52) U.S. Cl. ................ 424/499; 424/489; 424/499; 427/2.14
(58) Field of Search ................ 424/489, 499; 427/2.14

(56) References Cited

U.S. PATENT DOCUMENTS

| | | | |
|---|---|---|---|
| 3,915,800 A | * 10/1975 | Kang et al. ........... | 195/31 |
| 4,438,200 A | * 3/1984 | Taubman et al. ...... | 435/193 |
| 5,472,859 A | * 12/1995 | Brown, Jr. et al. ... | 435/101 |
| 5,576,015 A | 11/1996 | Donzis ................. | 424/442 |
| 5,961,970 A | * 10/1999 | Lowell et al. ........ | 424/93.1 |

FOREIGN PATENT DOCUMENTS

| | | |
|---|---|---|
| DE | 2737947 | 3/1978 |
| DE | 4120760 | 3/1993 |
| EP | 0476063 | 3/1992 |
| EP | 0648115 | 4/1995 |
| GB | 2247242 | * 2/1992 |
| WO | 88/08011 | 10/1988 |
| WO | 95/31553 | * 11/1995 |

OTHER PUBLICATIONS

Derwent Abstract of published Japanese appln. JP55001244B, (Kaken Yaku Kako KK), XP-002089601, (Jan. 12, 1980).

Derwent Abstract of published Japanese appln. JP51001372A, (Sumitoma Chem Co Ltd), XP-002089602 (Oct. 8, 1976).

* cited by examiner

Primary Examiner—Thurman K. Page
Assistant Examiner—S. Tran
(74) Attorney, Agent, or Firm—Connolly Bove Lodge & Hutz LLP

(57) ABSTRACT

Microparticles with a uniform spherical shape and a very narrow size distribution are described. They consist wholly or partly of a linear water-insoluble polysaccharide, preferably of 1,4-α-D-polyglucan, and may contain other, in particular biodegradable, polymers and/or active substances. They are suitable inter alia for the controlled delivery of active substances. They are prepared by dissolving 1,4-α-D-polyglucan or the polysaccharide in a solvent, introducing the solution into a precipitant, cooling the mixture and removing the particles formed.

6 Claims, 1 Drawing Sheet

10 μm

3 μm

SPHERICAL MICROPARTICLES CONTAINING LINEAR POLYSACCHARIDES

Figure 1:

The invention relates to spherical microparticles which contain linear polysaccharides, to processes for their preparation and to their use, in particular for controlled delivery of active substances.

Processes for preparing particles, especially microparticles from polymers such as, for example, polysaccharides, for a wide variety of applications are quite complicated processes which require accurate compliance with various parameters. In particular, many processes also result in only low yields and in very wide particle distributions. Mention should be made in this connection in particular of spray drying, interfacial condensation and emulsion processes (for example WO processes=water-in-oil emulsions, WOW= water-in-oil-in-water emulsions, coacervation, phase separation, dispersion). Emulsion processes in particular, but also spray dryings from two-phase systems, require a very accurate procedure and, in most cases, the use of auxiliaries (emulsifiers). Stable emulsions can often be prepared only at great expense and with precise control of a large number of parameters (temperature, stirring speed etc.), and comprehensive removal of the particles involves problems. The yield of particles is often very low and, in particular, the proportion of active substances entrapped is inadequate. This is as an aspect which may prevent application of a technology in the case of costly pharmaceutical active substances.

Spherical microparticles which, besides tartaric acid-containing polycondensates, which may also contain ethyl starch or other polysaccharides are obtained, according to U.S. Pat. No. 5,391,696, on the one hand by the spray-drying process, but with this the particle size and, in particular, the size distribution can be controlled only with great difficulty. Another possibility described in this patent is dissolving the polymer in a solvent or mixture of solvents and dropwise addition of the solution to a cold liquefied gas, for example liquid nitrogen, with formation of spherical particles. The small beads can then be introduced into water, which simultaneously precipitates the polymer and extracts the solvent. This process is time-consuming, costly and uneconomic. The uniformity of the particle dimensions is also unsatisfactory.

EP-B1-0 251 476 describes the preparation of microparticles from polylactides in which a macromolecular polypeptide is dispersed. Intensive control of a wide variety of parameters is necessary in this case too. Uniform spherical particles are not obtained.

Microparticles which contain active substances and gases are described in WO 95/07 072. Preparation takes place by elaborate emulsion processes, and the size distribution of the particles is very inhomogeneous.

Yu Jiugao and Liu Jie report in starch/stärke 46(7)252–5 (1994) on the effects of the suspension crosslinking reaction conditions on the size of starch microbeads. The crosslinking takes place in three stages; the medium is a water-in-oil suspension, and a peanut oil/toluene mixture is used as oil phase. Pregelatinized starch is added as aqueous solution which also contains sodium hydroxide and ethylenediamine-tetraacetic acid. The presence of a surface-active agent or stabilizer is also necessary.

The disadvantage of the process described therein is that the result depends on a large number of factors, namely on the density, the viscosity and the concentration ratios both of the aqueous and of the oil phase, on the stabilizer and on the stirring speed and, in addition, the presence of the stabilizer is disadvantageous. It is moreover difficult to control the large number of parameters given, so that the reproducibility is unsatisfactory.

Particles which are loaded with macromolecular active substances and are composed of water-insoluble polymers such as polylactic acid or ethylcellulose are obtained, according to the disclosure of EP-B1-0 204 476, by suspending the particulate active substance in an acetone solution of the polymer, and evaporating off the solvent at room temperature. The particles resulting in this case still do not show the required pharmacological effects, so that further processing to so-called pellets is necessary.

Although microparticles with a spherical shape and processes for preparing them are already known, there is still a need for such microparticles with improved properties, and for more advantageous, in particular economic and easily reproducible, preparation processes. It is therefore an object of the invention to provide microparticles which have a substantially regular spherical shape and which in addition show a size distribution which is as narrow as possible, i.e. a great uniformity, and which can be used for many purposes. Another object of the invention is to provide a process for preparing such microparticles which is simple and economic to carry out and which provides microparticles with regular structures and great uniformity, which have good mechanical properties, which are biodegradable, which can be provided with a wide variety of active substances, and which are particularly suitable for controlled delivery of active substances.

This object is achieved by spherical microparticles having an average diameter of from 1 nm to 100 $\mu$m, consisting wholly or partly of at least one water-insoluble, linear polysaccharide.

Spherical microparticles mean microparticles which have approximately a spherical shape. If a sphere is described by axes of equal length which are directed into space from a common origin and define the radius of the sphere in all directions in space, the length of the axes may deviate from the ideal spherical shape by from 1% to 40% for the spherical microparticles. Spherical microparticles with deviations of up to 25% are preferably obtained, particularly preferably up to 15%. The surface of the spherical microparticles can be compared macroscopically to that of a raspberry, it being intended that the depth of the "recesses" or "indentations" is not more than 20% of the average diameter of the spherical microparticles.

"Linear, water-insoluble polysaccharides" for the purpose of the present invention are polysaccharides which are composed of monosaccharides, disaccharides or other monomeric building blocks in such a way that the monosaccharides, disaccharides or other monomeric building blocks are always linked together in the same way. Each basic unit or building block defined in this way has exactly two linkages, in each case one to another monomer. Exceptions to this are the two basic units which form the start and end of the polysaccharide. These basic units have only one linkage to another monomer. When there are three linkages (covalent bonds), a branch is said to be present. Linear, water-insoluble polysaccharides for the purpose of the invention have no branches or, at the most, to only a minor extent, so that with very small proportions of branches they are not accessible to conventional analytical methods.

The term "water-insoluble polysaccharides" means for the present invention compounds which fall into the categories of 'sparingly soluble', 'slightly soluble', 'very slightly soluble'and 'practically insoluble' compounds as defined in the German Pharmacopeia (DAB=Deutsches Arzneibuch, Wissenschaftliche Verlagsgesellschaft mbH, Stuttgart, GoviVerlag GmbH, Frankfurt, 9$^{th}$ edition, 1987), corresponding to classes 4 to 7.

Preferred within the scope of the invention are linear, water-insoluble polysaccharides which have been prepared in a biotechnological, in particular in a biocatalytic, also biotransformation, or a fermentation process.

Linear polysaccharides prepared by biocatalysis (also: biotransformation) within the scope of this invention means that the linear polysaccharide is prepared by catalytic reaction of monomeric basic building blocks such as oligomeric saccharides, for example of mono- and/or disaccharides, by using a so-called biocatalyst, normally an enzyme, under suitable conditions.

Linear polysaccharides from fermentations are, in the terminology of the invention, linear polysaccharides which are obtained by fermentation processes using naturally occurring organisms such as fungi, algae or bacteria or using non-naturally occurring organisms but with the assistance of natural organisms which have been modified by genetic engineering methods as generally defined, such as fungi, algae or bacteria, or can be obtained with the involvement and assistance of fermentation processes.

Linear polymers according to the present invention may, besides the preferred 1,4-α-D-polyglucan, also be other polyglucans or other linear polysaccharides such as, for example, pullulans, pectins, mannans or polyfructans.

It is additionally possible to obtain linear polymers for preparing the microparticles described in the present invention also from reaction of other nonlinear polysaccharides by treating nonlinear polysaccharides which contain branches with an enzyme in such a way that cleavage of the branches occurs, so that linear polysaccharides are present after removal thereof. These enzymes may be, for example, amylases, isoamylases, gluconohydrolases or pullulanases.

In a particularly advantageous embodiment of the invention, the spherical microparticles consist wholly or partly of 1,4-α-D-polyglucan. The 1,4-α-D-polyglucan is preferably prepared by a biocatalytic (biotransformation) process using polysaccharide synthases or starch synthases or glycosyltransferases or α-1,4-glucan transferases or glycogen synthases or amylosucrases or phosphorylases.

The molecular weights $M_w$ of the linear polysaccharides used according to the invention may vary within a wide range from $10^3$ g/mol to $10^7$ g/mol. The molecular weights $M_w$ preferably used for the linear polysaccharide which is preferably used, 1,4-α-D-polyglucan, are in the range from $10^4$ g/mol to $10^5$ g/mol, in particular $2 \times 10^4$ g/mol to $5 \times 10^4$ g/mol.

It has now been found, surprisingly, that very uniform microparticles can be prepared in large quantities by a very simple process from water-insoluble linear polysaccharides, and cannot be obtained in this way from commercially obtainable polysaccharides such as, for example, amylose or starch.

The invention therefore also relates to a process for preparing spherical microparticles which consist wholly or partly of water-insoluble, linear polysaccharides, in particular 1,4-α-D-polyglucan, by dissolving the water-insoluble, linear polysaccharide or the 1,4-α-D-polyglucan in a solvent, introducing the solvent into a precipitant, cooling the mixture resulting therefrom, and removing the microparticles formed. Claims 20 to 23 specify particularly advantageous embodiments of the process according to the invention.

In another advantageous embodiment, the linear, water-insoluble polysaccharides have been prepared by enzymatic treatment of branched or highly branched polysaccharides.

Dimethyl sulfoxide is the preferred solvent for dissolving the linear polysaccharides; other possible solvents are, inter alia: formamide, acetamide, N,N-dimethylformamide, N,N-dimethylacetamide, N-methylmorpholine N-oxide in the presence of water, and other N-substituted morpholine N-oxides, aqueous solution with high or low pH.

Water is the preferred precipatant; the process can be influenced by using other solvents which are able to replace water wholly or partly, for example dichloromethane, it being possible to control inter alia the duration of the precipitation process and the texture of the surface of the particles. Mixtures of water with alcohols, for example methanol, ethanol, isopropanol, are also suitable for influencing the process parameters and the properties of the particles.

The temperature during the precipitation process is generally preferably in the range from 0° C. to –10° C., but higher or lower temperatures can also be taken.

The precipitation process can be carried out relatively slowly at low temperature overnight or be influenced by varying the precipitant and the temperature.

It is possible by also using suitable additives to exert an influence on the properties of the particles such as the size, the texture of the surface etc., and on the process controls. Examples of suitable additives are surface-active substances such as sodium dodecyl sulfate, or N-methylgluconamide, sugars, for example fructose, sucrose, glucose.

The surface-active substances may be anionic, cationic or nonionic in nature.

General examples of surface-active substances are: polysorbates (for example Tween®), alkyl polyglycoi ethers, ethylene oxide/propylene oxide block copolymers (for example Pluronic®), alkyl polyglycol ether sulfates, alkyl sulfates (for example the sodium dodecyl sulfate which has already been mentioned), fatty acid glycol esters. The additives are preferably added to the precipitant.

The concentration of the linear polysaccharide in the solution may be varied within wide limits but is preferably 0.1 g of polysaccharide per 1 ml of solvent.

Other ranges such as 0.05 g/ml to 0.2 g/ml or 0.02 g/ml to 0.5 g/ml are possible.

The particles according to the invention may consist of at least one linear polysaccharide and may contain at least one active substance. The surface can be smooth or rough.

The microparticles may be composed of a single linear polysaccharide substance, in particular 1,4-α-D-polyglucan. However, it is also possible to admix another linear water-insoluble polysaccharide. Other polymers, especially other biocompatible polymers, can also be used too. The quantity of the other polymer(s) which can be admixed without altering disadvantageously the spherical shape and other good properties of the microparticles always depends on the added polymer. It may be up to 10% or more, and less in certain cases. The maximum quantity which is still acceptable can easily be determined by a few mixing tests.

The particles may have average diameters (number average) such as 1 nm to 100 μm, preferably 100 nm to 10 μm, particularly preferably 1 μm to 3 μm.

The particles show a characteristic of the diameters $d_w$ to $d_n$ of (dispersity) 1.0 to 10.0, preferably 1.5 to 5.0, particularly preferably 2.0 to 2.6

$d_n$=number average diameter $d_w$=weight average diameter

The averages used herein are defined as follows:

$d_n = \Sigma n_i \times d_i / \Sigma n_i$=number average $d_w = \Sigma n_i \times d_i^2 / \Sigma n_i \times d_i$ = weight average $n_i$ = number of particles with diameter $d_i$, $d_i$ = a particular diameter, i = serial parameter.

The term "weight" does not in this case represent mass but represents a weighted mean. The larger diameters are given greater importance; the power of 2 gives greater weighting to diameters of larger particles.

The dispersity of the distribution of the diameters of the particles is defined as: $D = d_w/d_n$ The heterogeneity of the distribution of the diameters is defined as:

$$U = d_w/d_n - 1 = D - 1$$

A heterogeneity value closer to "0" means the particles are shaped more uniformly in respect of their size distribution. The microparticles can be employed advantageously, particularly also because of their uniform shape and size, in a wide variety of applications, either as such in pure form or by entrapping active substances in the widest sense, thus, for example,

- as additives for cosmetics in ointments, dusting powders, creams, pastes etc.,
- as vehicles for active substances in pharmaceutical and other applications,
- as smoothing agents, for example for closing pores or smoothing flashes,
- as food additive, for example as bulking component or for improving rheological properties,
- as additive for upgrading, for example, emulsion polymers,
- as separation aids, for example in the removal of impurities,
- as encapsulating material,
- as carrier for magnetic particles,
- as filler for biodegradable polymers or industrial polymers for controling properties,
- as additive for controling properties, for example the porosity, the weight, the color etc.,
- as particle standard for calibration or determination of the particle size of unknown materials.

Individual active substances or combinations of active substances can be found, for example, in the following list:
- pharmaceutical active substances, medicines, medicinal substances, peptides, proteins, nucleic acids, vaccines, antibodies, steroids, oligonucleotides, flavorings, perfumes, fertilizers, agrotechnical active substances such as pesticides, herbicides, insecticides, fungicides, chemicals with specific properties such as luminous materials, emulsifiers, surfactants, pigments, oxidants, reductants, fullerenes, magnetic complexes, for example paramagnetic compounds.

The invention thus also relates to the use of the microparticles described above for controlled, for example delayed, delivery of active substances.

The process comprises a very simple procedure. The parameters for preparing the particles can be specified within wide ranges, such as the ratio of solvent to precipitant, temperature during the precipitation process, concentration of the solution, rate of addition of the solution to the precipitant.

The particles are distinguished by a great uniformity in terms of their size and the distribution of their diameters.

The insolubility in water of the initial polymer, for example 1,4-α-D-polyglucan, makes it possible to implement particularly advantageous applications which are not out on a rapid destruction of the microparticles and can therefore also be used particularly advantageously in products in which water is present as another component.

The microparticles are distinguished by the ability to be exposed to high mechanical stressability.

In particular, because of their morphology and uniformity, the particles have a smoothing effect, for example on pores.

The 1,4-α-D-polyglucan which is preferably employed can be prepared in various ways. A very advantageous method is described in WO 95/131 553. The disclosure in this publication is incorporated herein by reference.

The invention is explained in detail by means of the following examples.

EXAMPLE 1

Preparation of Microparticles of 1,4-α-D-polyglucan 500 mg of 1,4-α-D-polyglucan are dissolved in 2.5 ml of dimethyl sulfoxide (DMSO, analytical grade, from Riedel-de-Haen) at about 70° C. The DMSO solution is added dropwise to 100 ml of double-distilled water with stirring, and the solution is kept at 5° C. overnight. The fine milky suspension is centrifuged at 3500 revolutions per minute for 15 minutes and the supernatant is decanted off. The sediment is suspended in double-distilled water and centrifuged again. The procedure is repeated two more times. The suspension is subsequently freeze-dried. 311 mg of white 1,4-α-D-polyglucan particles are obtained. This corresponds to a yield of 62% of colorless microparticles.

EXAMPLE 2

Attempt to Prepare Microparticles From Amylose Isolated From Plants 500 mg of amylose (from potatoes, from EGA-Chemie) are dissolved in 2.5 ml of dimethyl sulfoxide (DMSO, analytical grade, from Riedel-de-Haen) at about 70° C. The DMSO solution is highly viscous. It is added with stirring to 100 ml of double-distilled water, and the solution is kept at 5° C. overnight. A white flocculant suspension forms. The further processing takes place as described in Example 1. 210.3 mg of a white solid are obtained (42% yield) which comprises non-particulate structures.

EXAMPLE 3

Attempt to Prepare Microparticles From Amylose Isolated From Plants

This attempt is carried out in analogy to Example 2. 500 mg of amylose supplied by Merck (manufacturer's statement: "Amylose for biochemical purposes") are employed. After the period of standing overnight, a white flocculant suspension has formed. Further processing takes place as described in Example 1. 60 mg of a white solid are obtained (12% yield), with a very voluminous morphology and structure. Particulate structures are not found in this comparative example, in analogy to Comparative Example 2.

EXAMPLE 4 TO 8

Attempts to Prepare Microparticles From Starch Isolated From Various Plants 500 mg of starch (see Table 1 for specification) are dissolved in 2.5 ml of dimethyl sulfoxide (DMSO, analytical grade, from Riedel-de-Haen) at about 70° C. No solutions are formed. The mixtures form viscous gels. These are added with stirring to 100 ml of double-distilled water. The gel disintegrates during this. The solution is kept at 5° C. overnight. Very cloudy suspensions with a large number of large white flakes form. Further processing is carried out as described in Example 1. The results of the examples are listed in Table 1. It is evident with all the Comparative Examples 2 to 8 that the nonlinear polysaccharides or other starting materials differ very greatly from the results of the invention described in Example 1. Without exception there is formation of heavy turbidity and/or large flakes.

Structures with a particulate shape cannot be observed. In addition, the yields of solids in Comparative Examples 2 to 8 are distinctly less than in Example 1.

times. The solids are collected and the suspension of about 1000 ml is freeze-dried (Christ Delta 1–24 KD). 283 g of white solid are isolated (71% yield).

b) The collected supernatants are kept at a temperature of −18° C. overnight. Processing takes place as described. A further 55 g of the white solid are isolated (yield 15%).

The overall yield of this process is thus 85% of colorless microparticles.

EXAMPLE 10

Desulfurization of the Microparticles

The procedure for removing the dimethyl sulfoxide remaining in the particles is as follows. 100 g of the 1,4-α-D-polyglucan from Example 9 are added to 1000 ml

TABLE 1

Results of the precipitation of various starch/DMSO solutions in water

| Example | Starch type | Proportion of linear polysaccharide (%) | Consistency of the DMSO solution | Consistency of the suspension after precipitation at 5° C. | Final weight (mg) | Yield (%) |
|---|---|---|---|---|---|---|
| 1 | 1,4-α-D-Polyglucan *1 | 100 | clear, low-viscosity solution | fine, milky suspension | 311.0 | 62 |
| 2 | Amylose*2 (EGA-Chemie) | 90–100 | dissolved after 2 d, highly viscous | fine suspension with flakes | 210.3 | 42 |
| 3 | Amylose*2 (Merck) | 95–100 | dissolved after 2 d, highly viscous on heating | fine suspension with flakes | 60.0 | 12 |
| 4 | Potato Toffena ™ (Südstarke) | 20 | solid gel, clear | heavy turbidity | not separable (centrifuge) | — |
| 5 | Corn starch (Merck) | 20 | viscous gel | slight turbidity, large flakes | 83.8 | 17 |
| 6 | Corn starch C (National Starch) | 50 | viscous gel | heavy turbidity, small flakes | 101.7 | 20 |
| 7 | Corn starch HVII (National Starch) | 70 | viscous gel | heavy turbidity, small flakes | 211.1 | 42 |
| 8 | Peas (Amylose KG) | 70 | viscous gel, cloudy | heavy turbidity, large flakes | 115.9 | 23 |

*1 water-insoluble
*2 water-soluble

EXAMPLE 9a AND b

Preparation of Microparticles From 1,4-α-D-polyglucan on a Large Scale a) 400 g of 1,4-α-D-polyglucan are dissolved in 2 l of dimethyl sulfoxide (DMSO, analytical grade, from Riedel-de-Haen) over the course of 1.5 h at 60° C. The solution is then stirred at room temperature for one hour. The solution is added through a dropping funnel to 20 l of double-distilled water while stirring over a period of 2 h. The mixture is stored at 4° C. for 44 h. A fine suspension forms. The particles are removed by initially decanting off the supernatant. The sediment is suspended and centrifuged in small portions (RC5C ultracentrifuge: 5000 revolutions per minute for 5 minutes each). The solid residue is suspended in double-distilled water and centrifuged again a total of three of deionized water. The mixture is left for 24 h with gentle agitation. Removal of the particles takes place as described in Example 9 (RC5C ultracentrifuge: 3000 rpm for 15 minutes each). The final weight after freeze drying is 98.3 g (98% yield). Determination of sulfur by elemental analysis gives the following values (test method combustion and IR detection):

Sulfur content of the particles from Example 9: 6%+/−0.1%

Sulfur content of the particles from Example 10:<0.01%

EXAMPLE 11

Examination of the Solids From Examples 1 to 9 by Electron Microscopy

Figure 2:
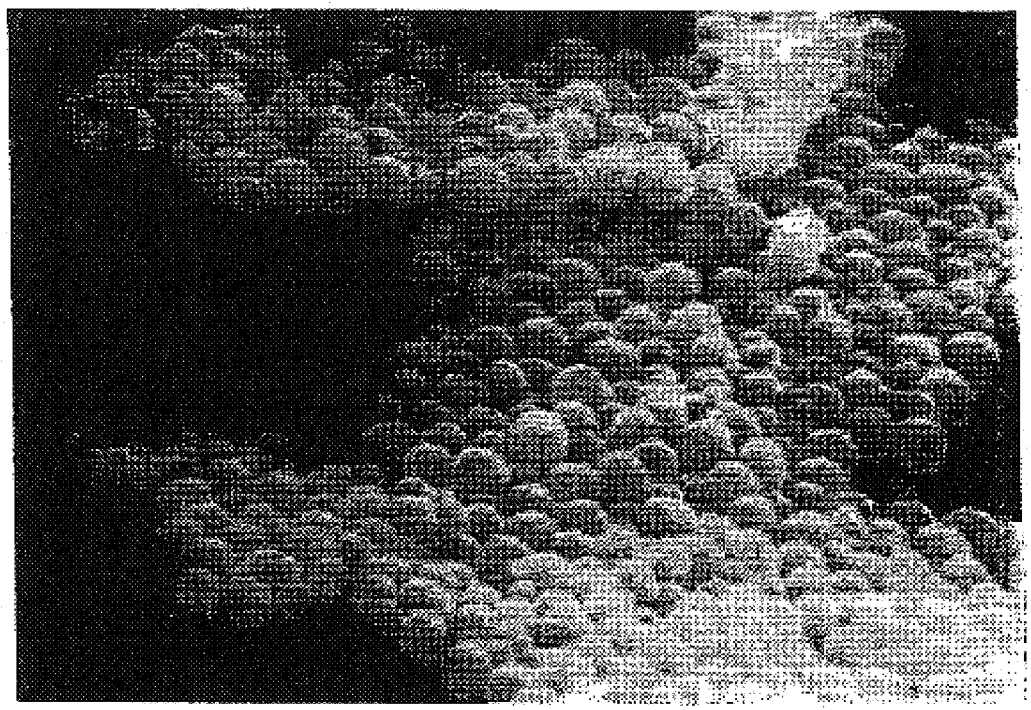

To characterize the particles, scanning electron micrographs (SEM) (Camscan S-4) are taken. The results of the examination are recorded in Table 2. It is clear from this that spherical microparticles are obtained only on use of water-insoluble linear polysaccharides (1,4-α-D-polyglucan). By contrast, the use of other initial polymers results only in voluminous, cottony and nonparticulate morphologies for which a dispersity cannot be determined. The structure of the particles obtained as in Example 1 is evident from FIGS. 1 and 2.

TABLE 2

Characterization of the solids and particles from Examples 1 to 3 and 7 to 9

| Example | Starch type | Proportion of linear polysaccharide (%) | Appearance of the particles |
|---|---|---|---|
| 1 | 1,4-α-D-Polyglucan*[1] | 100 | round separate particles |
| 2 | Amylose*[2] (EGA Chemie) | 90–100 | flocculant, voluminous, cottony (i.e. no separate particles) |
| 3 | Amylose*[2] (Merck) | 95–100 | flocculant, voluminous, cottony (i.e. no separate particles) |
| 7 | Corn Hylon VII (National Starch Chemistry) | 70 | flocculant, cottony (i.e. no separate particles) |
| 8 | Peas (Amylose KG) | 70 | flocculant, cottony (i.e. no separate particles) |
| 9a | 1,4-α-D-Polyglucan | 100 | round separate particles |
| 9b | 1,4-α-D-Polyglucan | 100 | round separate particles |

*[1]water-insoluble
*[2]water-soluble

EXAMPLE 12

Investigations of the Size Distributions of the Particles From Examples 1 and 9

Investigations are carried out with a Mastersizer (from Malvern Instruments) to characterize the size distributions of the particles from Examples 1 and 9. The investigation took place in the Fraunhofer mode (evaluation: multimodal, number) with a density of 1.080 g/cm$^3$ and a volume concentration in the range from 0.012% to 0.014%. The results of this investigation are listed in Table 3 and show the great uniformity of the microparticles.

EXAMPLE 13

In-vitro Production on 1,4-α-D-polyglucan in a Biocatalytic Process Using Amylosucrase 10 l of a 20% strength sucrose solution are placed in a sterilized (steam sterilization) 15 l vessel. The enzyme extract containing amylosucrase is added in one portion. The enzyme activity in this experiment amounts to 16 units. The apparatus is equipped with a likewise sterilized all-glass stirrer. The vessel is closed and kept at 37° C. with stirring. A white precipitate forms after a period of only a few hours. The reaction is stopped after a period of 180 hours. The precipitate is filtered off and washed five times with water to remove low molecular weight sugars. The residue remaining in the filter is dried in a drying oven at 40° C. under the vacuum of a diaphragm pump (CVC 2, Vacuubrand GmbH & Co). The mass amounts to 685 g (69% yield). The 1,4-α-D-polyglucan obtained in this way can be employed directly for characterization and for preparing microparticles.

EXAMPLE 14

Characterization of the Water-insoluble 1,4-α-D-polyglucan Synthesized With Amylosucrase From Example 13

2 mg of the 1,4-α-D-polyglucan from Example 13 are dissolved in dimethyl sulfoxide (DMSO, analytical grade, from Riedel-de-Haen) at room temperature and are filtered (2 µm filter). One portion of the solution is injected into a gel permeation chromatography column. DMSO is used as eluent. The signal intensity is measured by an RI detector and evaluated by comparison with a pullulan standard (supplied by Polymer Standard Systems). The flow rate is 1.0 ml per minute.

The measurement shows a number average molecular weight ($M_n$) of 14,200 g/mol and a weight average molecular weight ($M_w$) of 29,500 g/mol. This corresponds to a dispersity of 2.1.

TABLE 3

Characterization of the particle diameters from Examples 1 and 9

| | Diameter | | | Particle distribution | | |
|---|---|---|---|---|---|---|
| Example No. | $d_n$*[1] (µm) | $d_w$*[2] (µm) | $d_w/d_n$*[3] | d (10%)*[4] (µm) | d (50%)*[5] (µm) | d (90%)*[6] (µm) |
| 1 | 1.282 | 2.692 | 2.100 | 0.991 | 1.263 | 1.776 |
| 9a | 1.664 | 4.184 | 2.541 | 0.873 | 1.504 | 2.624 |
| 9b | 0.945 | 2.345 | 2.481 | 0.587 | 0.871 | 1.399 |

*[1]$d_n$: number average diameter
*[2]$d_w$: weight average diameter
*[3]$d_w/d_n$: dispersity of the particle diameters
*[4]d(10%): 10% of all particles have a diameter smaller than the stated value
*[5]d(50%): 50% of all particles have a diameter smaller than the stated value
*[6]d(90%): 90% of all particles have a diameter smaller than the stated value

What is claimed is:

1. A process for preparing spherical microparticles which consists essentially of wholly or partly of a water-insoluble linear 1,4-α-D-polyglucan of class 6 or 7 as defined in Deutsches Arzneibuch, which consists essentially of dissolving the water-insoluble linear 1,4-α-D-polyglucan in a solvent, introducing the solution into a precipitant, cooling the mixture resulting therefrom, and removing the microparticles formed and said solvent is dimethyl sulfoxide, formamide, acetamide, N,N-dimithylformamide, N,N-dimethylacetamide, N-methylmorpholine N-oxide or dichloromethane.

2. The process as claimed in claim 1, wherein said solution and said precipitant are mixed at temperatures from 20 to 50° C., and the mixture is cooled to temperatures from +10 to −100° C.

3. The process as claimed in claim 1, wherein said solvent is dimethyl sulfoxide.

4. The process as claimed in claim 1, wherein said precipitant is water or an aqueous medium.

5. The process as claimed in claim 1, wherein the solution is prepared in the presence of one or more biodegradable polymers and/or of one or more active substances.

6. The process as claimed in claim 1, wherein the mixture is cooled to temperatures from 5 to −5° C.

* * * * *

UNITED STATES PATENT AND TRADEMARK OFFICE
CERTIFICATE OF CORRECTION

PATENT NO. : 6,703,048 B1
DATED : March 9, 2004
INVENTOR(S) : Holger Bengs et al.

It is certified that error appears in the above-identified patent and that said Letters Patent is hereby corrected as shown below:

Column 10,
Line 50, "acetamnide" should read -- acetamide --.
Line 56, "-100º C." should read -- -10º C. --

Signed and Sealed this

Twenty-second Day of June, 2004

JON W. DUDAS
*Acting Director of the United States Patent and Trademark Office*